US011833306B2

(12) United States Patent
Heatherington

(10) Patent No.: US 11,833,306 B2
(45) Date of Patent: Dec. 5, 2023

(54) SELF-SANITIZING RESPIRATORY ASSEMBLY AND METHODS OF MAKING AND USING THE SAME

(71) Applicant: SNAP CPAP, LLC, Chapel Hill, NC (US)

(72) Inventor: Stuart Heatherington, Chapel Hill, NC (US)

(73) Assignee: SNAP CPAP, LLC, Chapel Hill, NC (US)

( * ) Notice: Subject to any disclaimer, the term of this patent is extended or adjusted under 35 U.S.C. 154(b) by 797 days.

(21) Appl. No.: 16/943,386

(22) Filed: Jul. 30, 2020

(65) Prior Publication Data

US 2020/0353195 A1 Nov. 12, 2020

Related U.S. Application Data

(63) Continuation of application No. PCT/US2019/016478, filed on Feb. 4, 2019.

(60) Provisional application No. 62/640,633, filed on Mar. 9, 2018, provisional application No. 62/627,800, filed on Feb. 8, 2018.

(51) Int. Cl.
  *A61M 16/06* (2006.01)
  *A61L 2/10* (2006.01)
  *A61L 2/20* (2006.01)

(52) U.S. Cl.
  CPC .......... *A61M 16/0666* (2013.01); *A61L 2/10* (2013.01); *A61L 2/202* (2013.01); *A61M 16/0622* (2014.02); *A61L 2202/24* (2013.01); *A61M 2205/02* (2013.01)

(58) Field of Classification Search
CPC .... A61M 16/0666–0677; A61M 16/08; A61M 16/0816; A61M 16/0875; A61M 16/0488–0497
See application file for complete search history.

(56) References Cited

U.S. PATENT DOCUMENTS

| 4,315,505 A * | 2/1982 | Crandall ........... A61M 16/0465 128/207.15 |
| 5,797,627 A * | 8/1998 | Salter .................... F16L 37/084 285/305 |
| 9,205,215 B2 | 12/2015 | McAuley et al. |
| 2005/0199242 A1 | 9/2005 | Matula et al. |

(Continued)

FOREIGN PATENT DOCUMENTS

| EP | 0821978 A2 | 2/1998 |
| EP | 3246064 A1 | 11/2017 |
| WO | 2005076874 A2 | 8/2005 |

OTHER PUBLICATIONS

EPO Action for corresponding EP Application 19750901.1 dated Mar. 28, 2023.

(Continued)

*Primary Examiner* — Rachel T Sippel
(74) *Attorney, Agent, or Firm* — NK Patent Law

(57) ABSTRACT

Nasal respiratory assembly includes flexible tubing connected to a fluid source. The flexible tubing includes a pair of receptacles through which the fluid is dispensed, a pair of posts, and a connector with a central opening sized and shaped to cooperate with one of the receptacles. Each post includes a flange sized and shaped to fit over the nostril of a patient; a main body comprising a passageway configured therein.

12 Claims, 14 Drawing Sheets

(56) References Cited

U.S. PATENT DOCUMENTS

| | | |
|---|---|---|
| 2009/0095303 A1 | 4/2009 | Sher et al. |
| 2009/0173349 A1 | 7/2009 | Hernandez et al. |
| 2013/0199537 A1* | 8/2013 | Formica ............ A61M 16/0622 |
| | | 128/205.25 |
| 2016/0022947 A1 | 1/2016 | Heatherington et al. |
| 2016/0206303 A1 | 7/2016 | Chaudhry et al. |
| 2017/0062677 A1 | 3/2017 | Okubo |
| 2017/0209300 A1* | 7/2017 | Radmand .......... A61M 16/0816 |
| 2017/0281966 A1 | 10/2017 | Basiony |

OTHER PUBLICATIONS

PCT, International Search Report and Written Opinion in International application No. PCT/US2019/016478 dated May 21, 2019.
PCT, International Preliminary Report on Patentability in International application No. PCT/US2019/016478 dated Aug. 11, 2020.
EPO, Partial Supplementary European Search Report for corresponding European Patent Application No. 19750901.1, dated Oct. 4, 2021, 12 pages.
EPO, Extended European Search Report for corresponding European Patent Application No. 19750901.1, dated Jan. 13, 2022, 10 pages.

* cited by examiner

SELF-SANITIZING RESPIRATORY ASSEMBLY AND METHODS OF MAKING AND USING THE SAME

CROSS-REFERENCE TO RELATED APPLICATIONS

This application is a continuation of International Patent Application No. PCT/US19/16478 filed on Feb. 4, 2019, which claims priority to U.S. Provisional Patent Application No. 62/627,800 filed on Feb. 8, 2018, and to U.S. Provisional Patent Application No. 62/640,633 filed on Mar. 9, 2018, the entire contents of which are incorporated by reference herein.

TECHNICAL FIELD

The presently disclosed subject matter relates to a respiratory assembly, and to methods of making, using and sanitizing the assembly.

BACKGROUND

Facial masks and nasal cannula are commonly used for treating patients with sleeping and/or breathing disorders. Particularly, high flow delivery of respirator gas can be delivered using nasal cannula and/or facial masks. Further, continuous positive airway pressure (CPAP) masks can deliver a treatment fluid (such as ambient air or oxygen-enriched air) to a patient under a predetermined or desired pressure setting. However, prior art masks and cannula are typically bulky, making them less aesthetically and ergonomically pleasing. Further, conventional masks and cannula must provide sealable engagement with the patient's skin, leaving unsightly wear marks that require significant amounts of time to dissipate. These depressions or marks can be the result of the masks enveloping the mouth and/or the nostril, as well as the straps or connections that typically positioned about the patient's head. In addition, due to the bulky nature of conventional masks and cannula, the patient's ability to move their head during sleep is affected. Particularly, when a patient lies on his side during sleep, the patient's pillow can contact and dislodge the mask, thereby evacuating the pressure in the mask assembly. As a result, the patient wakes up and/or does not receive treatment gases under the ideal pressure. It would therefore be beneficial to provide an improved respiratory assembly that addresses the disadvantages associated with conventional masks.

Additionally, if the CPAP masks are not cleaned after use, CPAP pathogens can build up in the CPAP assembly. As a result, a variety of health issues can arise, including pneumonia, bronchitis, infections, nasal passage irritation, and the like. Disinfecting wipes are commonly used to clean and deodorize CPAP masks and accessories. However, the wipes have been found to transfer bacteria and spores onto multiple surfaces. Alternately, soap and water are used to clean CPAP equipment. Unfortunately, this method is time consuming and inconvenient, since the user must take the CPAP equipment apart and wash each piece with soapy water. Further, it is nearly impossible to adequately clean every piece of a user's CPAP machine by hand, and even a small number of leftover pathogens can cause an infectious disease. It would therefore be further beneficial to provide an improved respiratory assembly that includes a sanitizer to disinfect the CPAP equipment.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

Disclosed herein is a nasal respiratory assembly comprising flexible tubing connected to a fluid source, wherein the flexible tubing comprises a pair of receptacles through which the fluid is dispensed; a pair of posts, and a connector with a central opening sized and shaped to cooperate with one of the receptacles. Each post comprises a flange sized and shaped to fit over the nostril of a patient; a main body comprising a passageway configured therein;

According to one or more embodiments, the flexible tubing has an inner diameter of about 2-4 mm.

According to one or more embodiments, each receptacle is configured to be inserted into the connector.

According to one or more embodiments, the fluid source is selected from a high flow generator, a continuous positive airway pressure (CPAP) machine, a fluid tank, or a humidifier.

According to one or more embodiments, the fluid is selected from a gas, a mixture of gases, or a gas with a medication.

According to one or more embodiments, the flange is angled.

According to one or more embodiments, the angle is between about 0 degrees and about 45 degrees.

According to one or more embodiments, the connector portion of the posts includes a ridge.

According to one or more embodiments, the receptacles each comprise a socket.

According to one or more embodiments, the socket comprises: a collar positioned at a first end; an adaptor positioned at a second end; a passageway extending from the first to the second ends; and a cavity positioned at the first end, sized and shaped to releasably house the connector and at least a portion of the post body therein.

According to one or more embodiments, the collar includes one or more releases that can be pivoted to maintain or release the post within the cavity.

Further disclosed herein is an oral assembly comprising an internal plate curved arcuately to fit in between the teeth and lips of a patient; an external plate curved arcuately to be positioned directly adjacent to an external surface of the mouth of the patient; a passageway extending through the internal plate and the external plate, wherein the passageway is releasably connected to a tubing that is connected to a fluid source; and a gasket in fluid connection to the passageway, the gasket comprising an aperture that connects to the tubing connected to the fluid source.

According to one or more embodiments, the internal plate is molded with an impression of the patient's top teeth, bottom teeth, or both the top and bottom teeth.

According to one or more embodiments, the passageway extends through the approximate center portion of the internal plate and the external plate.

According to one or more embodiments, the assembly lacks straps, masks, or both.

According to one or more embodiments, the internal plate comprises an upper segment and a lower segment connected via a hinge to allow movement of each segment in relation to the other.

According to one or more embodiments, the upper segment is molded to correspond to the shape of the upper teeth of the patient, the lower segment is molded to correspond to the shape of the lower teeth of the patient, or both.

According to one or more embodiments, a cushion is positioned between the external plate and the external surface of the patient's mouth.

According to one or more embodiments, the cushion is constructed from foam or silicone material.

According to one or more embodiments, the cushion has a central opening passing therethrough.

According to one or more embodiments, the gasket is positioned adjacent to the exterior plate, external to the patient's mouth.

According to one or more embodiments, the gasket comprises a swivel ring that allows connection to a fluid source, wherein the swivel ring allows the fluid source to swivel when connected.

According to one or more embodiments, the swivel ring comprises two branches, each branch including a socket positioned at a distal end.

Further disclosed herein is a respiratory assembly comprising a nasal assembly comprising flexible tubing including a pair of receptacles through which a fluid is dispensed; a pair of posts, each post comprising a flange sized and shaped to fit over the nostril of a patient; a main body comprising a passageway configured therein; a connector with a central opening sized and shaped to cooperate with one of the receptacles; and an oral assembly. The oral assembly comprises an internal plate curved arcuately to fit in between the teeth and lips of a patient; an external plate curved arcuately to be positioned directly adjacent to an external surface of the mouth of the patient; a passageway extending through the internal plate and the external plate, wherein the passageway is releasably connected to a gasket that is connected to a fluid source, the gasket in fluid connection to the passageway, wherein the gasket is in fluid connection to the receptacles of the flexible tubing of the nasal assembly.

Further disclosed herein is a method of providing a fluid to the nasal passages of a patient. The method comprises attaching a nasal assembly to the nares of a patient, the nasal assembly comprising: flexible tubing connected to a fluid source, wherein the flexible tubing comprises a pair of receptacles through which the fluid is dispensed; a pair of posts, each post comprising: a flange sized and shaped to fit over the nostril of a patient; a main body comprising a passageway configured therein; a connector with a central opening sized and shaped to cooperate with one of the receptacles; and initiating flow of the fluid source, wherein fluid flows from the fluid source to the flexible tubing to the receptacles to the passageways of the posts into the nasal passages of the patient.

Disclosed herein is a method of providing a fluid to the oral respiratory passages of a patient. The method comprises: attaching an oral assembly to the mouth of a patient, the oral assembly comprising: an internal plate curved arcuately to fit in between the teeth and lips of a patient; an external plate curved arcuately to be positioned directly adjacent to an external surface of the mouth of the patient; a passageway extending through the internal plate and the external plate, wherein the passageway is releasably connected to tubing that is connected to a fluid source; and a gasket in fluid connection to the passageway, the gasket comprising an aperture that connects to a tubing of a fluid source; connecting the gasket to a fluid source; initiating flow of the fluid source, wherein fluid flows from the fluid source to the gasket to the passageway to the oral respiratory passages of the patient.

Disclosed herein is a method of providing a fluid to the nose and mouth of a patient. The method comprises: attaching an oral assembly to the mouth of a patient, the oral assembly comprising: an internal plate curved arcuately to fit in between the teeth and lips of a patient; an external plate curved arcuately to be positioned directly adjacent to an external surface of the mouth of the patient; a passageway extending through the internal plate and the external plate, wherein the passageway is releasably connected to tubing that is connected to a fluid source; and a gasket in fluid connection to the passageway, the gasket comprising an aperture that connects to a tubing of a fluid source; and attaching a nasal assembly to the nares of a patient. The nasal assembly comprises: flexible tubing in fluid connection to the gasket, the flexible tubing including a pair of receptacles through which the fluid can flow through; a pair of posts, each post comprising: a flange sized and shaped to fit over the nostril of a patient; a main body comprising a passageway configured therein; a connector with a central opening sized and shaped to cooperate with one of the receptacles; and connecting the gasket to the fluid source; and initiating flow of the fluid source, wherein fluid flows from the fluid source to the gasket and then into two gasket branches, wherein the first branch comprises the passageway to the oral respiratory passages of the patient and the second branch is in fluid connection to the flexible tubing of the nasal assembly of the patient.

Further disclosed herein is a self-sanitizing nasal respiratory assembly. The assembly comprises: flexible tubing connected to a fluid source, wherein the flexible tubing comprises a pair of receptacles through which the fluid is dispensed; a pair of posts, each post comprising: a flange sized and shaped to fit over the nostril of a patient; a main body comprising a passageway configured therein; a connector with a central opening sized and shaped to cooperate with one of the receptacles; and an enclosure. The enclosure comprises: a pair of opposing sidewalls, a front wall, a rear wall, a bottom wall, and a top lid that define an interior; a generator positioned within the interior, wherein the generator is capable of generating activated oxygen, UV light, or both; an aperture configured in a sidewall of the enclosure, sized and shaped to house the flexible tubing.

According to one or more embodiments, the lid is attached to the rear wall through one or more mechanical elements.

According to one or more embodiments, the mechanical element comprises a hinge.

According to one or more embodiments, the aperture is positioned adjacent to the lid.

According to one or more embodiments, the UV light has a wavelength of about 100-280 nanometers.

According to one or more embodiments, the generator produces activated oxygen at a concentration of about 10-500 parts per million.

According to one or more embodiments, the flexible tubing has an inner diameter of about 2-4 mm.

According to one or more embodiments, the enclosure is attached to the fluid source.

According to one or more embodiments, the generator comprises a built-in timer that controls the release of activated oxygen, UV light, or both.

Disclosed herein is a method of sanitizing a respiratory assembly. The method comprises: depositing a pair of receptacles and a portion of flexible tubing of a respiratory assembly into an interior of an enclosure. The respiratory assembly comprises: flexible tubing connected to a continuous positive airway pressure device, wherein the flexible tubing comprises a pair of receptacles through which fluid is dispensed; a pair of posts, each post comprising: a flange sized and shaped to fit over the nostril of a patient; a main body comprising a passageway configured therein; and. a connector with a central opening sized and shaped to cooperate with one of the receptacles. The enclosure comprises: a pair of opposing sidewalls, a front wall, a rear wall, a bottom wall, and a top lid that define an interior; a generator positioned within the interior, wherein the generator is capable of generating activated oxygen, UV light, or both; an aperture configured in a sidewall of the enclosure, sized and shaped to house the portion of the flexible tubing; and initiating the production of activated oxygen, UV light, or both within the interior of the enclosure. The generated activated oxygen, UV light, or both travels from the interior of the enclosure, through the flexible tubing to a continuous positive airway pressure device in fluid communication to the flexible tubing, whereby the respiratory assembly is sanitized.

According to one or more embodiments, the lid is attached to the rear wall through one or more mechanical elements.

According to one or more embodiments, the mechanical element comprises a hinge.

According to one or more embodiments, the aperture is positioned adjacent to the lid.

According to one or more embodiments, the UV light has a wavelength of about 100-280 nanometers.

According to one or more embodiments, the generator produces activated oxygen at a concentration of about 10-500 parts per million.

According to one or more embodiments, the flexible tubing has an inner diameter of about 2-4 mm.

According to one or more embodiments, the enclosure is attached to the continuous positive airway pressure device.

According to one or more embodiments, the generator comprises a built-in timer that controls the release of activated oxygen, UV light, or both.

According to one or more embodiments, the enclosure is permanently or removably attached to the continuous positive airway pressure device.

According to one or more embodiments, wherein sanitizing of the respiratory assembly commences automatically when the top lid is closed.

According to one or more embodiments, the top lid automatically unlocks after sanitizing of the respiratory assembly is completed.

According to one or more embodiments, the continuous positive airway pressure device is connected to the respiratory assembly when the sanitizing of the respiratory assembly is underway.

According to one or more embodiments, the enclosure further comprises an indicator light that illuminates when the sanitizing process is underway.

BRIEF DESCRIPTION OF THE DRAWINGS

The foregoing, as well as the following Detailed Description of preferred embodiments, is better understood when read in conjunction with the appended drawings. For the purposes of illustration, there is shown in the drawings exemplary embodiments; however, the presently disclosed subject matter is not limited to the specific methods and instrumentalities disclosed.

The embodiments illustrated, described, and discussed herein are illustrative of the present invention. As these embodiments of the present invention are described with reference to illustrations, various modifications or adaptations of the methods and or specific structures described may become apparent to those skilled in the art. It will be appreciated that modifications and variations are covered by the above teachings and within the scope of the appended claims without departing from the spirit and intended scope thereof. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

FIG. 3b is a side cutaway view of the post of FIG. 3a.

FIG. 5b is a side cutaway view of the socket receptacle of FIG. 5a.

FIG. 7b is a side cutaway view of the assembly of FIG. 7a.

FIG. 8b is a side plan view of the enclosure of FIG. 8a.

DETAILED DESCRIPTION OF THE EMBODIMENTS

Figure 1A:
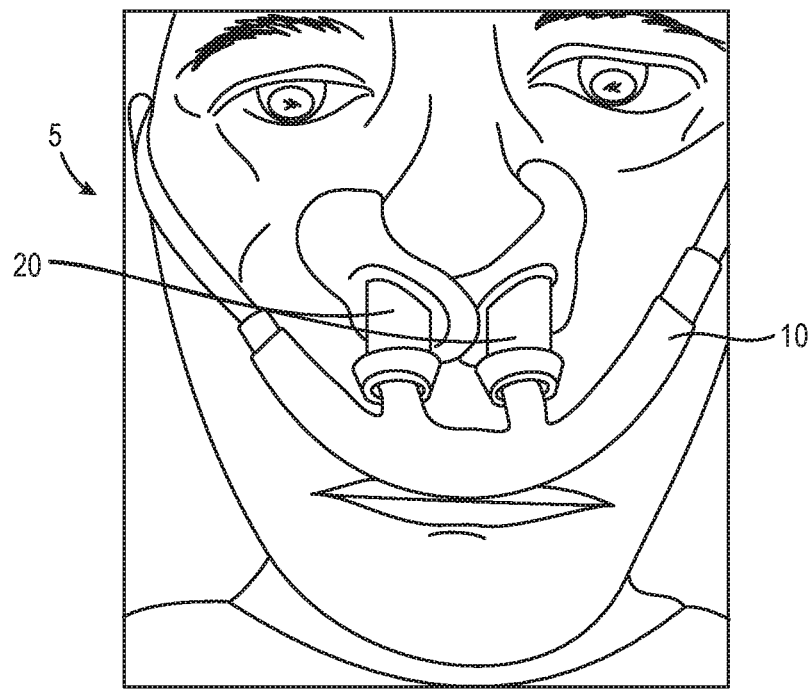
FIGS. 1a and 1b are perspective views of a nasal respiratory assembly in accordance with some embodiments of the presently disclosed subject matter.

Below, the technical solutions in the examples of the present invention are depicted clearly and comprehensively with reference to the figures according to the examples of the present invention. Obviously, the examples depicted here are merely some examples, but not all examples of the present invention. In general, the components in the examples of the present invention depicted and shown in the figures herein can be arranged and designed according to different configurations. Thus, detailed description of the examples of the present invention provided in the figures below are not intended to limit the scope of the present invention as claimed, but merely represent selected examples of the present invention. On the basis of the examples of the present invention, all of other examples that could be obtained by a person skilled in the art without using inventive efforts will fall within the scope of protection of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

These and other changes can be made to the disclosure in light of the Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description of The Embodiments section explicitly defines such terms. Accordingly, the actual scope of the disclosure encompasses not only the disclosed embodiments, but also all equivalent ways of practicing or implementing the disclosure under the claims.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments+/−20%, in some embodiments+/−10%, in some embodiments+/−5%, in some embodiments+/−1%, in some embodiments+/−0.5%, and in some embodiments+/−0.1%, from the specified amount, as such variations are appropriate in the disclosed packages and methods.

Figure 1B:
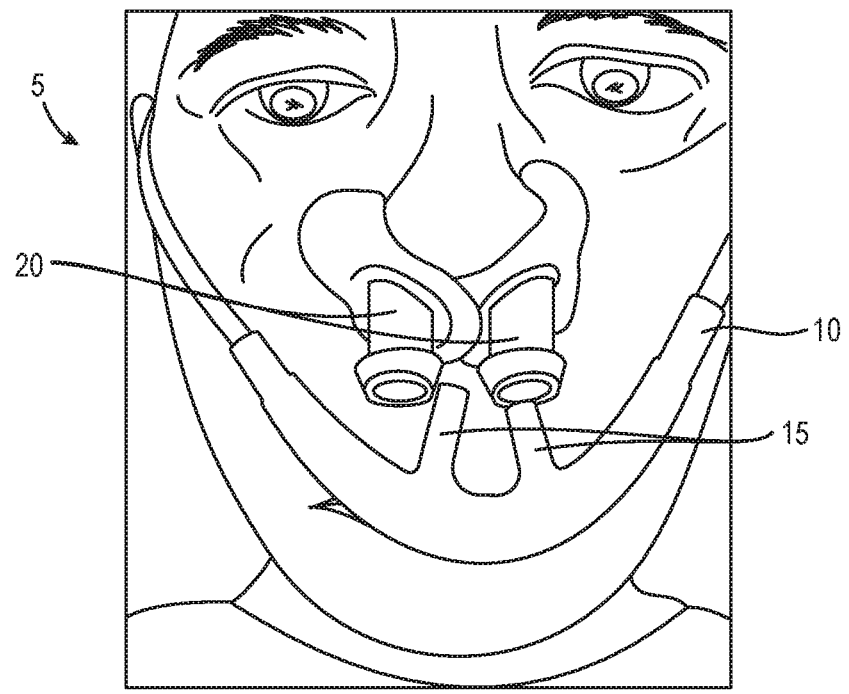

The presently disclosed subject matter is directed to a respiratory assembly, and further to the sanitization of the respiratory assembly. FIGS. 1a and 1b illustrate one embodiment of nasal assembly 5 installed upon a patient. As shown, nasal assembly 5 comprises flexible tubing 10 that includes at least one receptacle 15 for delivering treatment gases to the nasal cavity of a patient. The nasal assembly further includes posts 20 that are configured to engage the nares (i.e., nostrils) of the patient. In some embodiments, the receptacles are configured as prongs that are inserted into posts 20. Tubing 10 has an inlet connected to a fluid source (not shown) that provides the respiratory gas. In some embodiments, the fluid source can be a high flow generator, a continuous positive airway pressure (CPAP) machine, a fluid tank, a humidifier, or any other fluid source known or used in the art. The term "fluid" as used herein refers to any gas, mixture of gases, or gas with medication (such as an aerosol medication) suitable for delivery to the airway of a human.

Tubing 10 can include any known flexible tubing. The term "tubing" as used herein refers to any conduit, a delivery conduit, a tube, pipe, passage, or channel through which fluid flows. The term "flexible" as used herein refers to any tubing that is able to flex or bend and that is compliant and will readily conform to the general shape and contours of the human body. In some embodiments, tubing 10 can be constructed from medical grade materials, such as (but not limited to) polyurethane, polyvinyl chloride, polyamide, polyester, polyolefin, silicone, fluoropolymer, and combinations or copolymers thereof. The tubing is flexible, resilient, and hollow. In some embodiments, the tubing can have an inner diameter of between about 2-4 mm, although tubing with larger or smaller diameters can be used. For example, the inner diameter of the tubing can be increased or decreased to adjust for a particular wearer's preferences and/or needs. In use, tubing 10 can be hooked over the ears of a patient and can brought up under the chin during use.

Figure 2:
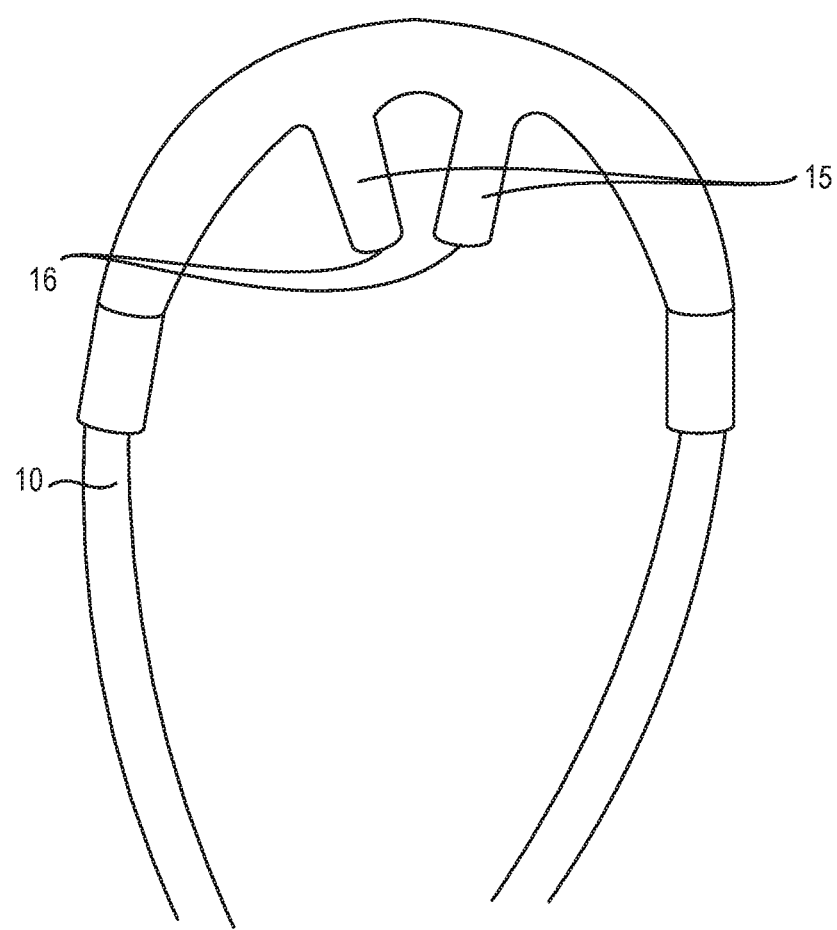
FIG. 2 is a perspective view of tubing that can be used with the disclosed assembly in some embodiments.

As shown in FIG. 2, tubing 10 can include a short pair of radially-directed receptacles 15 configured as nasal prongs that extend into the nostrils of the wearer and are removably engageable with posts 20. In some embodiments, the receptacles are parallel or about parallel to each other. The nasal receptacles are in fluid communication with the interior of the tubing, such that respiratory fluid flows from exit end 16 of each receptacle. Thus, each nasal receptacle comprises a unique pathway for conveying fluid from the inner tubing to the nasal passage of the patient. The receptacles can have various shapes, such as a circular, oval or rectangular in cross-section.

Figure 3A:
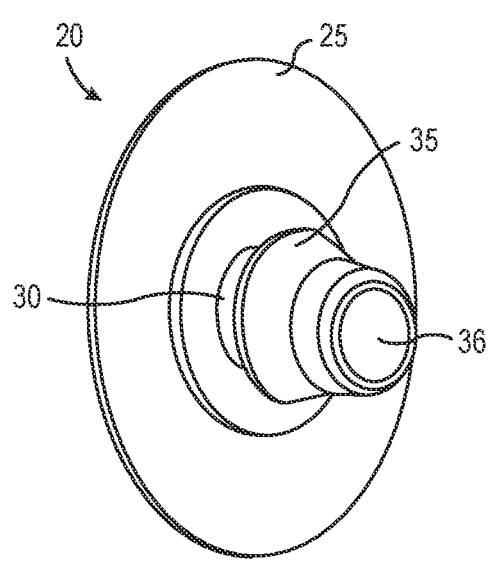
FIG. 3a is a perspective view of a post that can be used with a nasal respiratory assembly in accordance with some embodiments of the presently disclosed subject matter.
Figure 3B:
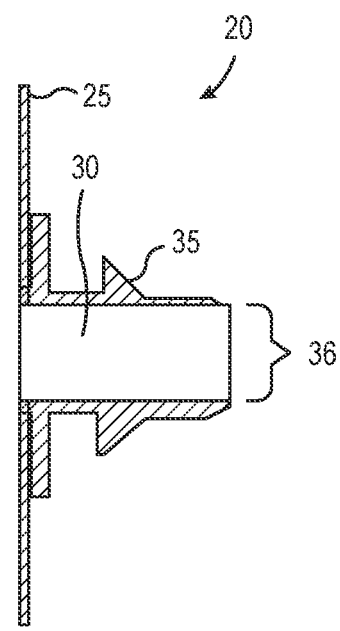
Figure 3C:
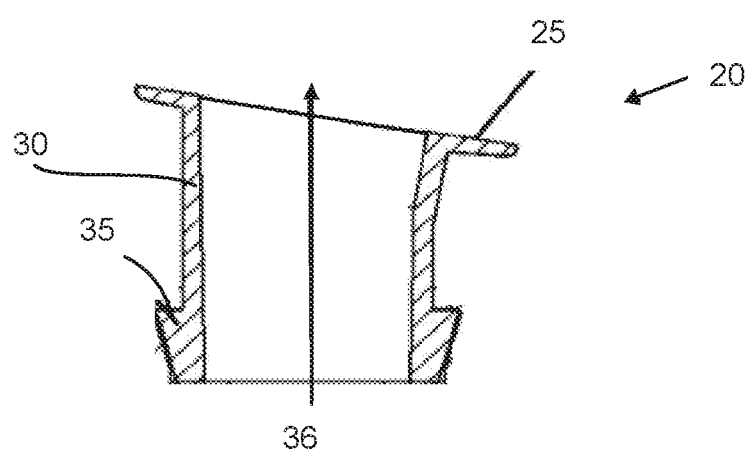
FIG. 3c is a side cutaway view of a post that can be used with a nasal respiratory assembly in accordance with some embodiments of the presently disclosed subject matter.

In some embodiments, nasal assembly 5 includes a pair of posts 20. Particularly, receptacles 15 cooperate with posts 20 that are configured to engage the nostrils of the patient. The posts can be configured for providing a flush, sealable engagement with the patient's nares. As shown in FIGS. 3a-3c, post 20 comprises flange 25 that directly contacts the exterior of a patient's nostril or the skin surrounding the patient's nostril, body 30, and connector 35. As shown, the interior of post 20 includes channel 36 passing through the entire length thereof to allow fluid flow to the nasal cavity of the patient. Interior channel 36 is sized and shaped to allow for insertion of a receptacle during use.

Figure 3D:
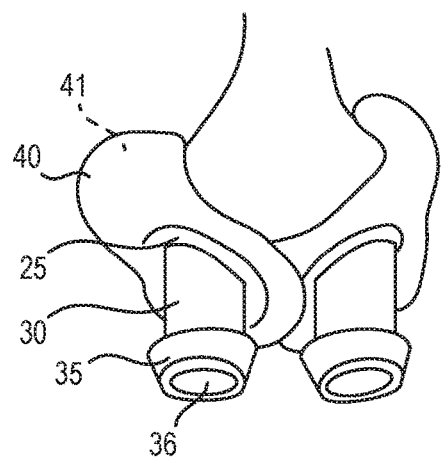
FIG. 3d is a perspective view of the post of FIG. 3c in use.

Flange 25 is configured about a first end of the post. In some embodiments, the flange engages with one or more flexible adhesive sheets 40 to provide sealable engagement with the patient's nostrils, as shown in FIG. 3d. Sheet 40 can be constructed from any known material, including (but not limited to) woven fabric, plastic, and/or latex. For example, in some embodiments, sheet 40 can be constructed from PVC, polyethylene, polyurethane, latex, or combinations thereof. In some embodiments, sheet 40 can be a foam medical tape, a surgical tape, and/or a hypoallergenic tape. The patient contacting surface of sheet 40 can include adhesive 41. The adhesive can be any medically-safe adhesive known or used in the art. For example, the adhesive can be selected from one or more acrylates (such as methacrylate, alkyl acrylate, or epoxy diacrylate), acrylic acids, polyvinyl chloride, alkyl esters, or combinations thereof. In some embodiments, the adhesive is a pressure-sensitive adhesive such that the sheet can be adhered and removed from the patient's skin as desired. The adhesive can be selected to show mild or no irritation to the skin when used daily. In some embodiments, the adhesive tape can be configured as a hydrocolloid tape and/or can include a polyurethane reactive layer that adheres more to the nostril as the patient's body temperature warms up the adhesive. Alternatively, in some embodiments, adhesive 41 can be directly applied to the patient's nostril or the nasal engaging portion to provide a removeable connection (e.g., no sheet is used).

As shown in FIG. 3c, flange 25 can be angled in relation to body 30 to allow for enhanced positioning on the patient's nostrils. In some embodiments, the angle can be between about 0-45 degrees, such as about 5, 10, 15, 20, 25, 30, 35, 40, or 45 degrees. In some embodiments, the angle can be created by having a portion of the post body bulge outwards at an angle. Alternatively, body 30 can remain substantially cylindrical, having a top portion cut at an angle.

Body 30 houses channel 36 within its interior to allow the flow of fluid to the nasal cavity of the patient. In some embodiments, body 30 can have a circular, oval or square cross-sectional shape. However, the shape of body 30 is not limited and can be configured in any desired shape. Further, channel 36 can have any desired cross-sectional shape, such as square, triangular, circular, oval, and the like.

In some embodiments, post 20 further includes connector 35 configured on a second post end for engaging receptacle 15 and/or a socket. In some embodiments, connector 35 can comprise a tapered ridge, as illustrated in FIGS. 3a-3d. However, the shape of the connector is not limited, and can be constructed to enable insertion of receptacle 15 and/or to enable connection with one or more sockets, as set forth in more detail herein below. In some embodiments, connector 35 can be configured to selectively engage a receiving portion on a receptacle. The engagement of the connector with the receptacle can be achieved using a number of different structural configurations. For example, connector 35 can be a circumferentially extending portion for selectively engaging a respective recess-receiving portion on a receptacle. Alternatively, the connector can be a ball joint and the receiving portion can be a tube socket, as set forth in more detail herein below.

In some embodiments, post 20 can include one or more vents in communication with channel 36 to ensure that the patient's ability to breathe is not hampered, and to ensure excess fluid has an outlet. The vents can be sized and shaped in any desired configuration and can be positioned proximal to any of the regions where fluid flow occurs. Thus, the vents can be positioned on the flange, body, and/or connector of the post. The vents can vary in size and location such that manipulation of all exhaled fluids (e.g., $CO_2$) is controlled and titratable to alter the flow rate to a desired setting. In some embodiments, the vents can include polymeric fibers, membranes, and/or webs with an extremely small thickness (e.g., from nanoscale to microscale).

Post 20 can be constructed from any desired material. For example, the post can be constructed from rubber, silicone polymers, acrylate polymers, or combinations thereof. It should be appreciated that the materials used to construct post are not limited to the materials cited herein above.

Figure 4A:
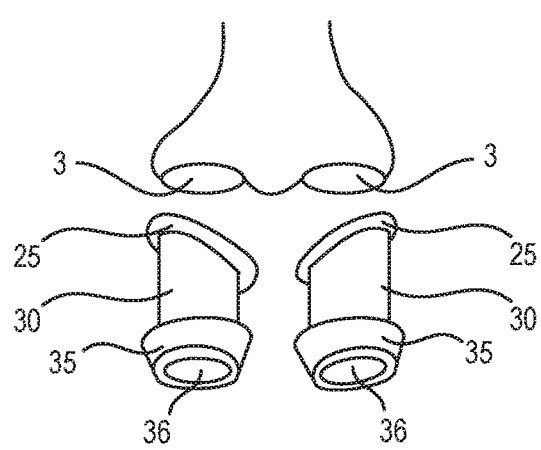
FIGS. 4a-4d are perspective views illustrating one embodiment of assembling the nasal respiratory assembly.
Figure 4B:
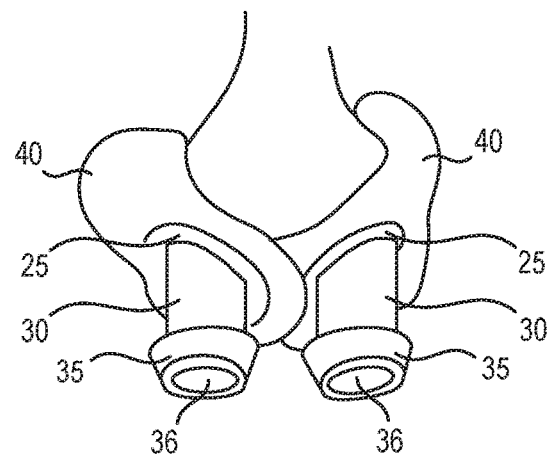
Figure 4C:
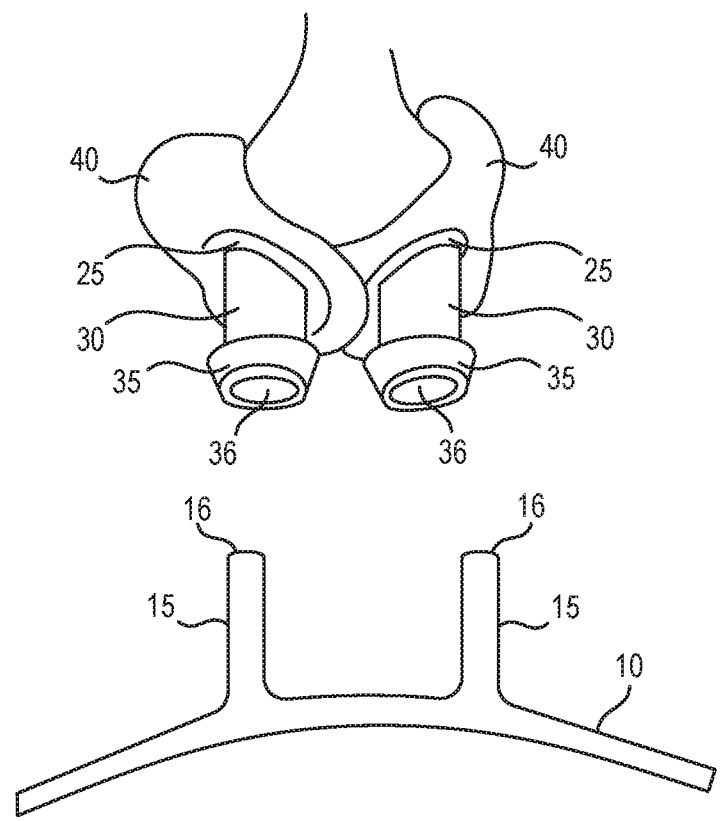
Figure 4D:
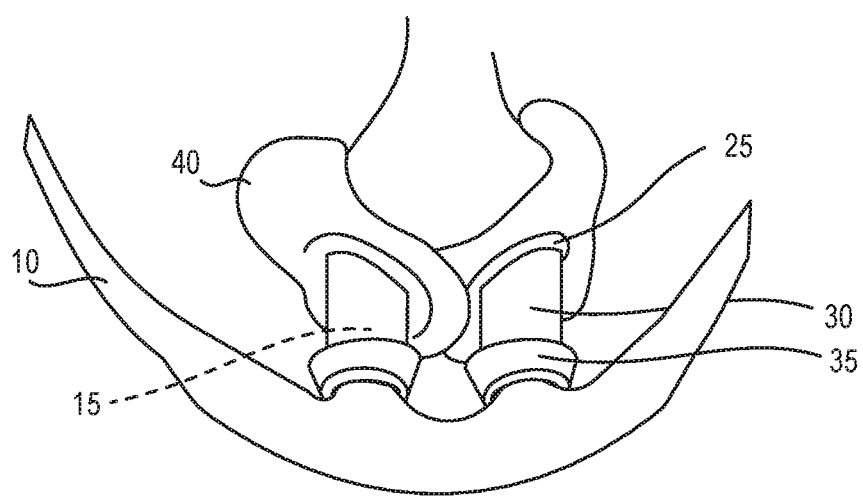

FIGS. 4a-4d illustrate one method of using post 20. Particularly, a post can be attached to the exterior portion of each patient nostril 3 by affixing post flange 25 directly to the skin surrounding the nostril. In this arrangement, post channel 36 is positioned in line with the nostril opening. In some embodiments, sheet 40 comprising adhesive 41 can be used can be used to attach the flange to the nostril, as illustrated in FIGS. 4a and 4b. Thus, the adhesive side of the sheet can be used to adhere flange 25 to the skin of the patient. Alternatively, adhesive 41 can be directly applied to the patient's skin (e.g., the area surrounding the nostril) or to the flange without the use of sheet 40. The post can be configured for providing a flush, sealable engagement with the patient's nostril. After a post has been affixed to the exterior portion of each of the patient's nostrils, receptacle 15 of tubing 10 can be translated towards channel 36 at the second end of the post. As shown in FIGS. 4c and 4d, open exit ends 16 (gas-flow end) of the receptacle is inserted at least partially into channel 36. Fluid flows from the tubing, through the interior of the receptacle, exits the receptacle via exit end 16 and flows to channel 36 and into the patient's nasal passages.

Figure 5A:
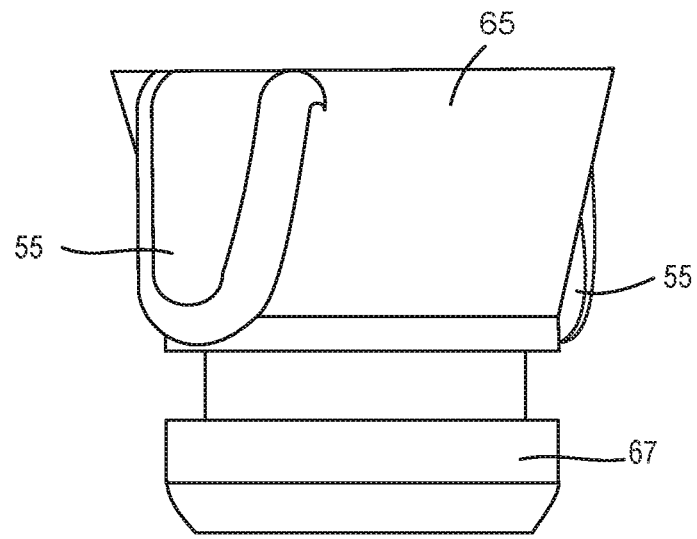
FIG. 5a is a perspective view of one embodiment of a socket receptacle that can be used in accordance with the presently disclosed subject matter.
Figure 5B:
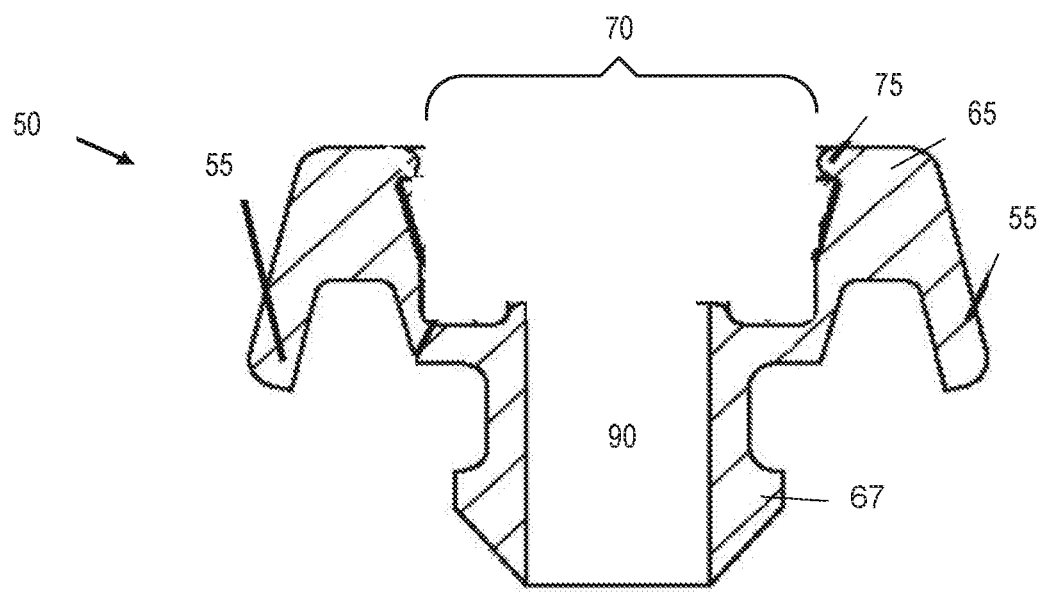

In some embodiments, tubing receptacles 15 can be configured as sockets 50 that releasably connect with posts 20. Specifically, as shown in FIGS. 5a and 5b, socket 50 can include one or more releases for engaging and disengaging the post from the socket. The release can include any of the wide variety of connection mechanisms known or used in the art, including (but not limited to) snap fit, screw fit, friction fit, magnetic attraction, and the like. For example, in some embodiments, the release can be configured as one or more arms 55 that extend from collar end 65 of the socket. The arms can be constructed at an angle to provide leverage when pivoting the arm, thereby enabling socket collar end 65 to be deformed away from the post positioned in socket cavity 70 for easy release. The socket further includes adaptor 67 positioned at the end distal from collar end 65. Adaptor 67 includes channel 90 that connects with socket cavity 70 to allow the flow of fluid from the tubing to reach the post. The adaptor can be constructed in any desired shape to allow connection with tubing 10. In such embodiments, the outer diameter of adaptor 67 is greater than the inner diameter of tubing 10. In this way, the adaptor is held within the tubing for a desired amount of time, and cannot be accidentally unlodged by the patient, such as during sleep. However, the adaptor can be releasably connected to tubing 10 using any known mechanism.

Figure 5C:
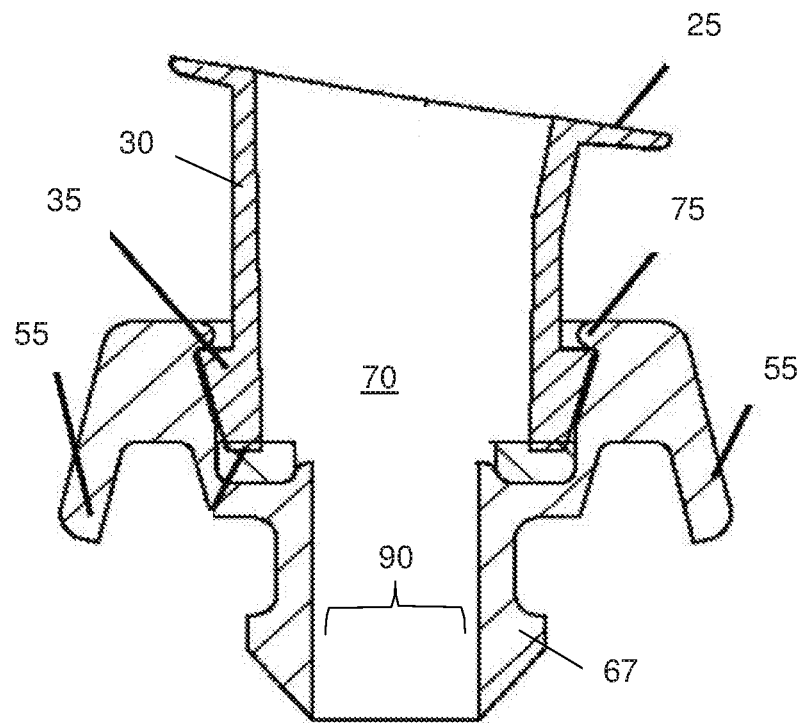
FIG. 5c is a side cutaway view of the socket receptacle of FIG. 5a in use.

As shown in FIG. 5c, at least a portion of post 20 is housed within a socket recess such as socket cavity 70. For example, the socket recess can be configured to house post connector 35 and at least a portion of body 30. The socket recess can permit deformation of the socket when the release is activated. Particularly, in embodiments comprising arms 55, the recess can allow for deformation of the socket when the arms are pivoted. In some embodiments, socket cavity 70 extends through collar end 65 of the socket and/or can extend horizontally beneath the collar for permitting deformation of a left or right half of the collar when the arms are pivoted. As shown in FIG. 5c, pivoting can involve placing pressure on one or more arms 55, either individually or simultaneously, so that the arms are flexed towards adaptor 67, thereby lifting collar bead 75 and releasing connector 35 of post 20. In this way, the tubing socket can be releasably attached to the post to allow for better retention and ease of use.

Figure 5D:
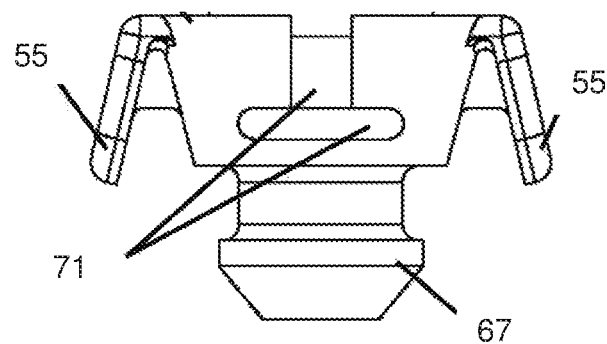
FIG. 5d is a perspective view of a socket receptacle in accordance with some embodiments of the presently disclosed subject matter.

In some embodiments, socket 50 can include one or more vents 71 positioned proximal to where fluid flow occurs, as illustrated in FIG. 5d. It should be appreciated that vents 71 can be positioned at any desired location and are not limited to the locations illustrated herein.

To position the post within the socket, a user simply translates connector 35 of the post towards socket cavity 70, such that the connector is retained within the cavity. For example, the connector can be advanced within the socket cavity, towards adaptor 67, until the collar bead is positioned between the post body and the connector. In some embodiments, arms 55 are pivoted to allow the post to be properly positioned within the socket (e.g., the allow the connector to fit within the socket cavity such that collar bead 75 is positioned between body 30 and the connector. In some embodiments, the connector portion includes a ridge or other similarly-shaped element that is maintained within the cavity. However, it should be appreciated that the presently disclosed subject matter is not limited, and the socket cavity can retain the connector using any known mechanism.

Figure 6:
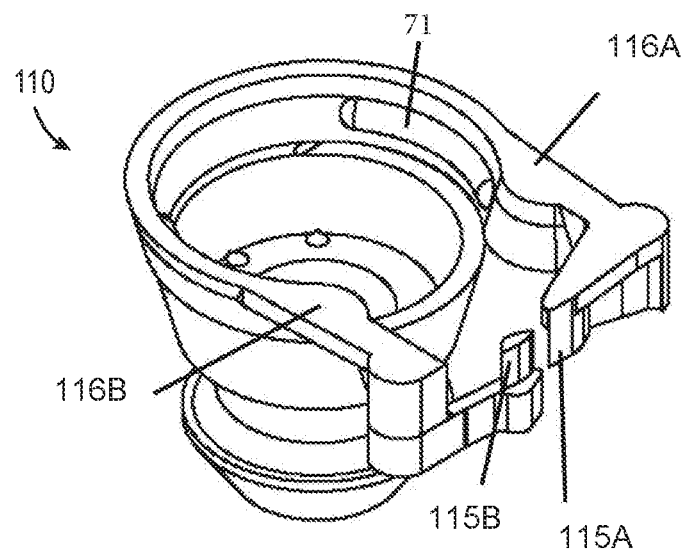
FIG. 6 is a perspective view of one embodiment of a socket receptacle that can be used in accordance with the presently disclosed subject matter.

FIG. 6 illustrates one embodiment of socket 50 comprising a clamp lock. Particularly, clamp lock 110 can include two clamp extensions. The first clamp extension 115A can define first clamp mound 116A and second clamp extension 115B can define second clamp mound 116B. One or both of the clamp mounds can include a clamp ridge for permitting the clamp mounds to be lockingly engaged when clamp extensions 115A 115B are pinched together. Once engaged, clamp mounds 116A, 116B can be disengaged with the application of pressure (e.g., a subsequent pinch). In some embodiments, clamp extensions 115A 115B together engages connector 35 for securing the post in position. In some embodiments, post 20 can include one or more small protrusions on the underside of the post, distal from the flange for further securing the post in position and resisting rotation of the post.

In use, a post can be attached to the exterior portion of each nostril by affixing flange 25 directly to the skin surrounding the nostril, as set forth in detail herein above. Socket 50 in connected arrangement with tubing 10 is then translated towards the post such that post connector is positioned in socket cavity 70. The post connector (which in some embodiments can be configured as a ridge) can be held in place by the socket release (e.g., arms 55). When a user desires to uncouple the post and socket, the arms are pivoted to allow the post to freely exit the socket recess. In some embodiments, arms 55 are manipulated away from the connector and towards the bottom portion of the socket to move bead 75 away from the connector. Alternatively, in embodiments where in the socket includes one or more clamp mounds 116, the clamps can be opened to release the connector ridge.

The presently disclosed subject matter includes two examples of sockets that can be used with the disclosed respiratory assembly. However, it should be appreciated that further embodiments and modifications of the sockets are included within the scope of the presently disclosed subject matter.

Figure 7A:
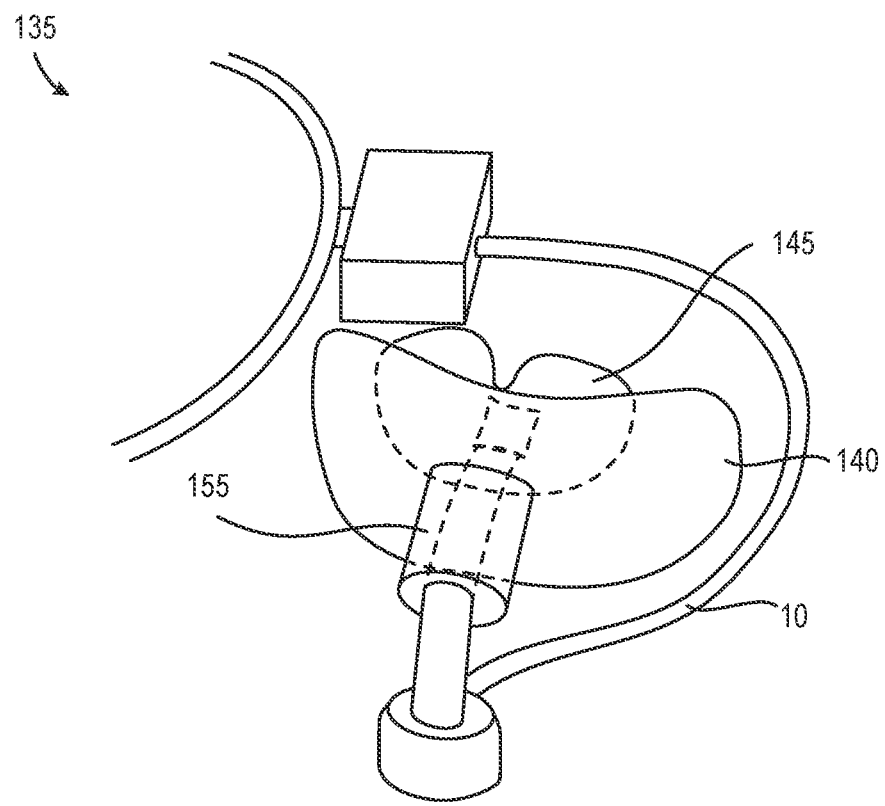
FIG. 7a is a perspective view of one embodiment of an oral respiratory assembly in accordance with some embodiments of the presently disclosed subject matter.
Figure 7B:
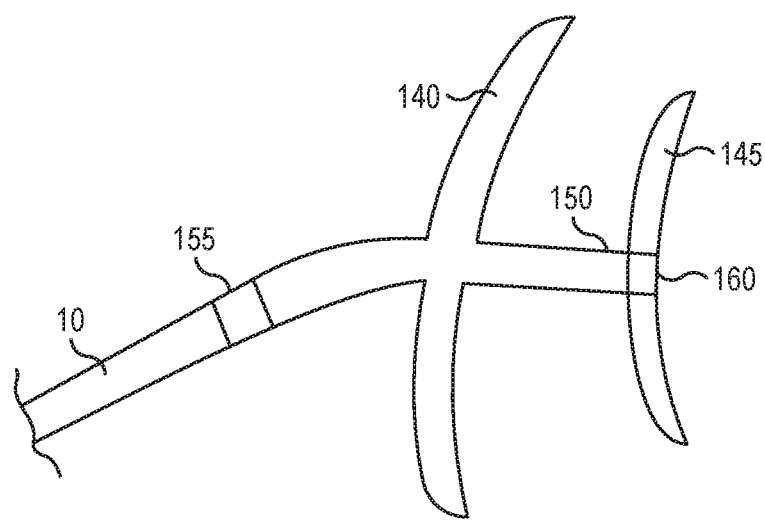

In some embodiments, the presently disclosed subject matter can include an oral respiratory assembly. Particularly, as shown in FIGS. 7a and 7b, oral assembly 135 can comprise passageway 150 in fluid connection with tubing 10. Passageway 150 can be configured as a tube or channel that passes through external and internal plates 140, 145 to deliver a fluid directly to the oral airway of the patient. As shown, external plate 140 is configured to be positioned on the exterior of the patient's mouth, and internal plate 145 is configured to be positioned between the patient's lips and teeth. Tubing 10 is connected to a fluid source. Fluid flows from the fluid source via tubing 10 and through the passageway to reach the airway of the patient.

Internal plate 145 can be constructed of a size and shape to fit between the lips and the teeth of the patient. The internal plate projects upwardly and downwardly from passageway 150 and is curved arcuately to comfortably fit within the mouth interior. In some embodiments, the internal plate can be molded to the shape of the upper teeth, lower teeth, or both the upper and lower teeth. Passageway 150 extends through internal plate 145 via exit 160 which functions as an exit, allowing respiratory air to enter the patient's airway. In some embodiments, the passageway extends through the approximate center portion of the internal plate. Passageway 150 can be constructed as a portion of tubing or other channel that allows the influx of air. In some embodiments, the oral assembly 135 can include separable joint 155 between the tubing and the mouthpiece assembly to allow the patient to remove the assembly for cleaning and/or for replacement with a new oral assembly. Joint 155 can include any known mechanism to attach and remove the mouthpiece assembly, such as a snap fit, screw fit, friction fit, and/or magnetic mechanism.

External plate 140 can be constructed of a size and shape to fit over the patient's mouth, adjacent to the exterior portion of the lips. The external plate projects upwardly and downwardly from passageway 150 and can be curved arcuately to be comfortably positioned on the exterior of the patient's lips. Passageway 150 extends through external plate 140. In some embodiments, the passageway extends through the approximate center portion of the external plate.

The internal and external plates can be constructed from a wide variety of materials, such as (but not limited to) rubber, silicone polymers, acrylate polymers, and combinations thereof. In some embodiments, the materials used to construct the fittings can be selected for medical use.

Figure 7C:
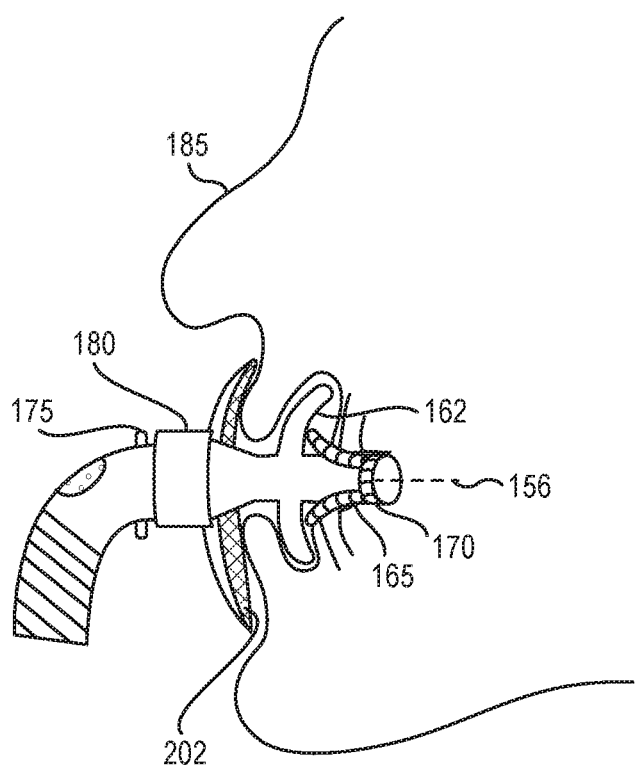
FIG. 7c is a side cutaway view of an oral assembly in accordance with some embodiments of the presently disclosed subject matter.

FIG. 7c illustrates one embodiment of oral assembly 135 that includes an optional interior mouth guard 156 that can be form-fit to the patient's teeth on the interior of the oral apparatus. In some embodiments, the mouth guard can include upper portion 162 and lower portion 165 configured on either side of hinge 170 (or any other mechanism that allows the upper and lower portions to move relative to each other) to allow the patient to move his jaw. As shown in FIG. 7c, the assembly can include quick connect release 175 over the front of the mouth comprising engagement 180. In some embodiments, the engagement can be a swivel engagement, as shown in FIG. 7c. However, the presently disclosed subject matter is not limited to a swivel engagement and any type of engagement mechanism can be used. The engagement can hold a connector that includes sockets 50 that lead up to the patient's nose 185 and attaches to posts 20 that are adhered to nostrils 3.

Figure 7D:
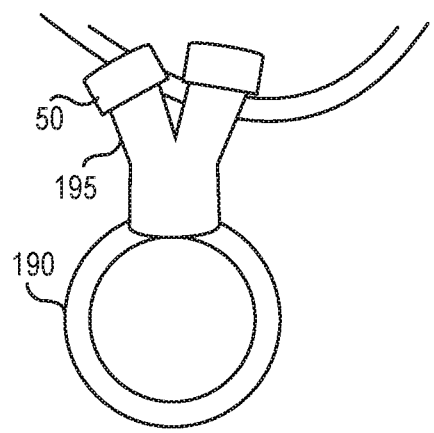
FIG. 7d is a swivel ring that can be used the oral assembly of FIG. 7e.

As shown in FIG. 7d, the assembly can include swivel ring 190 comprising a connector tubing such as branched tubing 195 that is connected to sockets 50. As set forth in detail herein above, the sockets releasably connect with posts 20 attached to patient nostrils 3.

Figure 7E:
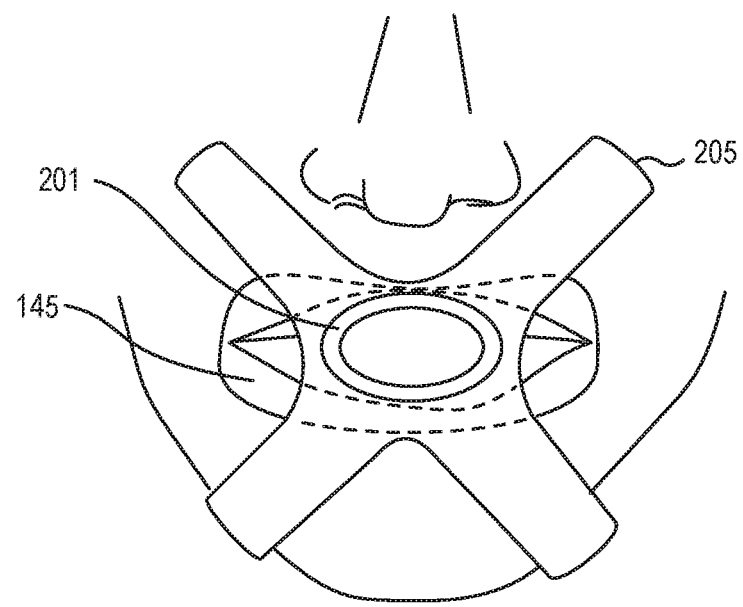
FIG. 7e is a front plan view of a mouthpiece that can be used with an oral assembly in accordance with some embodiments of the presently disclosed subject matter.

In some embodiments, the oral assembly can include foam layer 202 positioned between the patient's lips and device external plate 140 to help the device seal against the skin and to increase user comfort during use. The foam layer 202 can be created in any desired shape, such as round with central aperture 201 to allow fluid to pass into the patient's oral passageway. In one embodiment, foam layer 202 can be a cushion. As shown in FIG. 7e, tape 205 can be used to surround the exterior plate against the skin. For example, the tape can cross over the mouth in a variety of ways to create a seal.

Figure 7F:
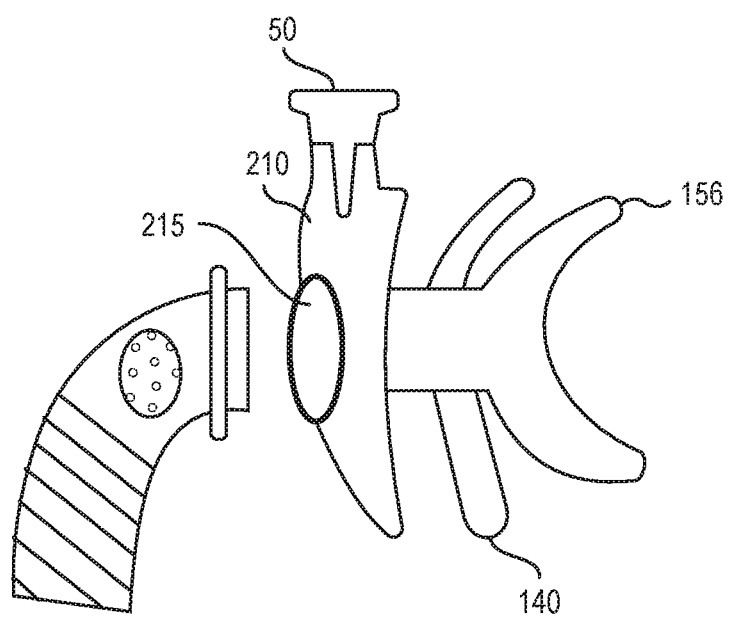
FIG. 7f is a side plan view of an oral assembly comprising a connection to a fluid source in accordance with some embodiments of the presently disclosed subject matter.

FIG. 7f illustrates a further embodiment of oral assembly 135 capable of releasably attaching to a fluid source (such as the tubing of a CPAP machine). Particularly, the oral assembly includes hollow gasket 210 that can be constructed from a wide variety of materials, such as (but not limited to) silicone. In some embodiments, the gasket can form a part of external plate 140, as shown in FIG. 7f. The gasket is connected to interior and exterior plates via passageway 150. The gasket includes recess 215, sized and shaped to connect to the fluid source. In some embodiments, the gasket and the fluid source tubing can be connected by snap fit, screw fit, friction fit, or magnetic attachment.

In use, oral assembly 135 can be connected to tubing 10 to allow the flow of fluid from a fluid source, through the tubing and into the mouthpiece. The internal plate is then inserted into the patient's oral cavity, between the patient's teeth and lips. The external plate is positioned against the exterior of the patient's mouth, directly adjacent to the patient's lips. In some embodiments, a sheet comprising an adhesive can be used to attach external plate 140 to the patient's mouth. Alternatively, an adhesive can be directly applied to the patient's skin (e.g., in areas near the mouth opening and the lip) or to the skin-facing side of the external plate without the use of a sheet. In this way, the oral assembly remains properly positioned and does not shift or fall out of the mouth. Fluid then flows from the fluid source, through tubing 10 and into the mouthpiece assembly. Particularly, fluid flows from the tubing and into passageway 150, through the first and second plates to exit 160 into the patient's oral cavity.

When the patient desires to remove the mouthpiece assembly, he simply removes the exterior plate from his lips by grasping the sheet and removing it from the exterior plate. The patient is then free to remove the mouthpiece from his mouth. The mouthpiece can be removed from the tubing for cleaning and/or replacement through joint 155.

It should be appreciated that the oral and nasal assemblies can be used alone or in conjunction with each other. For example, the respiratory assembly can include a nasal cannula fitted with one or more posts and/or gaskets and can be directly connected to a fluid source. In some embodiments, the respiratory assembly can include an oral assembly (e.g., mouthpiece or a mask) that is directly connected to a fluid source. Alternatively, the respiratory assembly can include a nasal assembly and an oral assembly used in conjunction, such as through a joint connection to a gasket.

Accordingly, the respiratory assembly described herein has three distinct modes of operation: one in which treatment gases are being supplied to the patient's mouth only, one in which treatment gases are being supplied to the patient's nose only, and one in which treatment gases are being supplied to the patient's nose and mouth.

The respiratory assembly disclosed herein has a wide variety of applications. For example, in some embodiments, the assembly can be used for high flow delivery of respirator gas via nasal cannula. In some embodiments, the air can be heated to near body temperature (e.g., about 37° C.) and/or humidified (e.g., about 100% relative humidity) to decrease airway moisture loss, airway cooling, nasal irritation, and the like. In high flow therapy, the source of oxygen is typically blended with compressed air, allowing the delivery of air, blends of air and oxygen from about 22% to about 99%, or delivery of 100% oxygen with the use of an oxygen blender. Advantageously, the disclosed assembly includes tubing large enough to deliver flow rate of respiratory gas of up to about 50 liters per minute for adults. The nasal cannula is also small enough to prevent sealing of the nares, allowing flow during exhalation and allowing the escape of excess gas during inhalation. Beneficially, because the delivered flow rate can meet the inspiration flow rate, the delivered gases are not diluted by room air.

Alternatively or in addition, the disclosed respiratory assembly can be used with a continuous positive airway pressure (CPAP) machine. CPAP machines typically apply mild air pressure on a continuous basis to keep a patient's airway continuously open. As a result, CPAP machines used in conjunction with a patient's stent can advantageously cause the lungs' alveoli to open and thus recruit more of the lung's surface area for ventilation. CPAP machines are generally used for people with breathing problems, such as sleep apnea. Alternatively, CPAP machines can be used to treat pre-term infants whose lungs have not yet fully developed. In some embodiments, the disclosed assembly can be used as a replacement for traditional CPAP masks.

The disclosed respiratory assembly can further be used in pressure recording applications in clinical settings, such as to diagnose sleep apnea or other disorders. Particularly, sleep apnea can be diagnosed based on characteristic clinical features associated with episodes of cessation of breathing that define hypopnoeic and apnoeic events. The disclosed device can be used to measure nasal pressure by measuring nasal pressure with nasal prongs connected to a pressure transducer.

The disclosed assembly can further be used with a fluid tank, a humidifier, or any other fluid source known or used in the art.

Advantageously, the disclosed assembly may eliminate over-the-ear soreness and lip soreness commonly found in traditional respiratory masks and cannula. In addition, the disclosed assembly may enable better control of gases (e.g., oxygen) during fluid delivery applications.

In some embodiments, the disclosed assembly is strapless and maskless, thereby increasing using comfort. As a result, patients are more likely to follow doctor's orders and use the assembly. In addition, unsightly mask and strap skin indentations are eliminated.

The disclosed assembly is less likely to be dislodged inadvertently by the patient, such as during movement or when being pressed against a pillow.

Figure 8A:
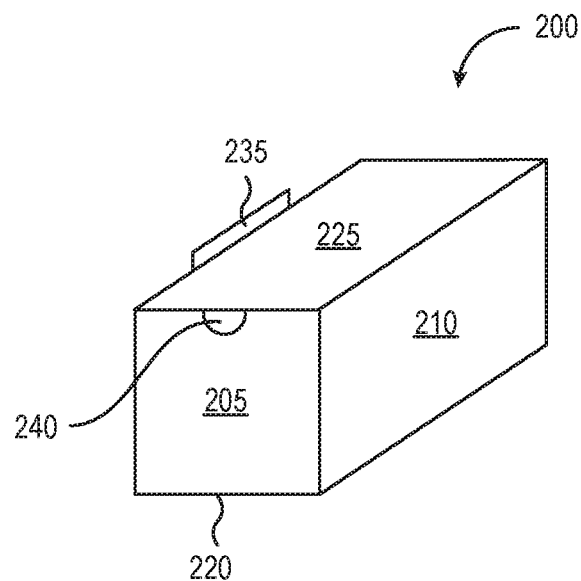
FIG. 8a is a perspective view of a sterilizing enclosure in accordance with some embodiments of the presently disclosed subject matter.
Figure 8B:
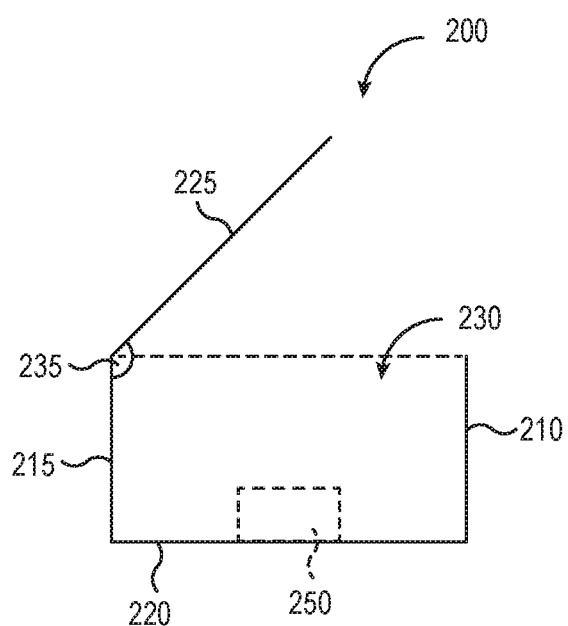

Referring to FIGS. 8a and 8b, in some embodiments, the disclosed respiratory assembly includes a sanitizing enclosure that can be used to sanitize the reusable portions of the CPAP assembly. The term "sanitizing" as used herein refers to the elimination of all or nearly all microbial forms. As shown in FIGS. 8a and 8b, enclosure 200 can be defined by a pair of opposing sidewalls 205, opposing front and rear walls 210, 215, bottom wall 220, and hinged lid 225 disposed on the top of the enclosure for providing access to interior 230. It should be appreciated that lid 225 can be attached to the enclosure using any mechanical element, and is not limited to hinges 235. In some embodiments, the lid can be completely removed from the enclosure. Sidewalls 205 and/or front wall 210 can include aperture 240 positioned adjacent to the lid. The aperture is sized and shaped to allow attached tubing 245 (see FIGS. A and 9b) to pass from the interior through the sidewall when the lid is closed, as shown, for example, in FIG. 9b. Aperture 240 can allow a tight fit with tubing 245 such that no UV light and/or activated oxygen generated within the enclosure interior can escape during sanitizing applications.

As illustrated in FIG. 8b, enclosure 200 includes an activated oxygen and/or UV light generator 250 that is used to clean and/or sanitize the reusable CPAP elements. For example, in some embodiments, generator 250 can generate activated oxygen to sanitize the contents of interior 230 and the reusable CPAP system, as discussed in detail below. Activated oxygen (also known as O3 or ozone) is a safe, naturally-occurring gas that has been shown to kill virtually all known forms of viruses in water and air. Particularly, activated oxygen has been shown to interfere with the metabolism of bacterium cells, likely through inhibiting and blocking the operation of the enzymatic control system. A sufficient amount of activated oxygen breaks through the cell membrane, leading to destruction of the bacteria. Activated oxygen destroys viruses by diffusing through the protein coat into the nucleic acid core, resulting in damage to the viral RNA. At higher concentrations, activated oxygen destroys the viral capsid by oxidation to affect the DNA or RNA structure. Activated oxygen has been shown to be effective in destroying dozens of harmful pathogens, including *E. coli*, influenza virus, *Staphylococcus, Streptococcus* bacteria, Stomatitis virus, and many more.

In some embodiments, generator 250 can produce activated oxygen in a concentration of about 10-500 ppm (parts per million) within the interior and/or within the disclosed system.

In some embodiments, generator 250 can produce UV light to sanitize the contents of interior 230 and the associated CPAP equipment. To this end, generator 250 can include one or more ultraviolet lights that can be activated for a pre-set time period. UV light is highly effective at deactivating microorganisms, including bacteria, viruses, yeasts, and molds. In some embodiments, the UV light is in the range of about 100-280 nanometers which is known to damage the DNA molecules in bacteria, viruses, molds, yeasts, and other microorganisms, preventing them from replicating and causing harm.

Figure 9A:
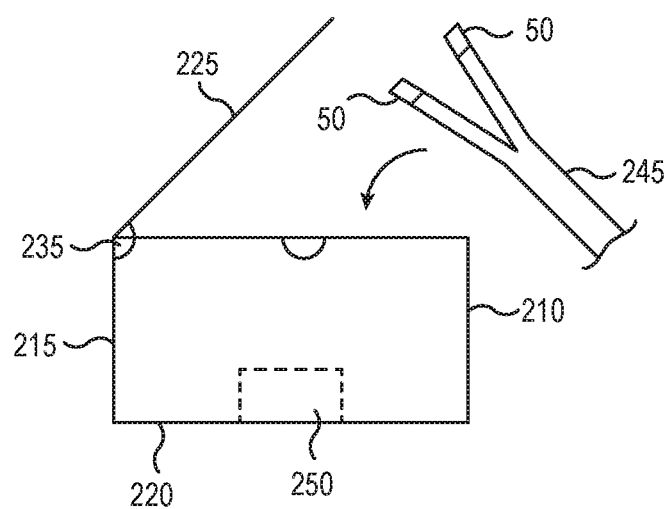
FIGS. 9a-9c are side plan views of the enclosure of FIG. 8a during use.
Figure 9B:
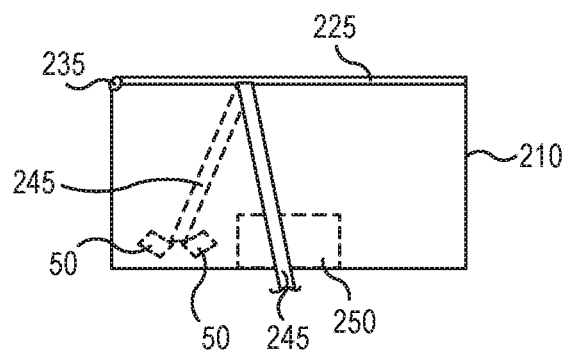

In use, one or more reusable portions of the CPAP assembly can be positioned within enclosure interior 230. For example, as shown in FIG. 9a, lid 225 can be opened and sockets 50 connected to tubing 245 can be positioned within enclosure interior 230. Tubing 245 can be positioned to extend from the enclosure interior, through aperture 240, to the exterior of the enclosure, and the lid can then be closed, as shown in FIG. 9b. In one embodiment, tubing 245 can be a flexible tubing. Generator 250 can then be activated to generate ozone and/or UV light to sanitize the contents of interior 230 (e.g., sockets 50). In some embodiments, closing of lid 225 automatically triggers activation of generator 250. Alternatively, the generator can be programmed to delay start of activation.

Figure 9C:
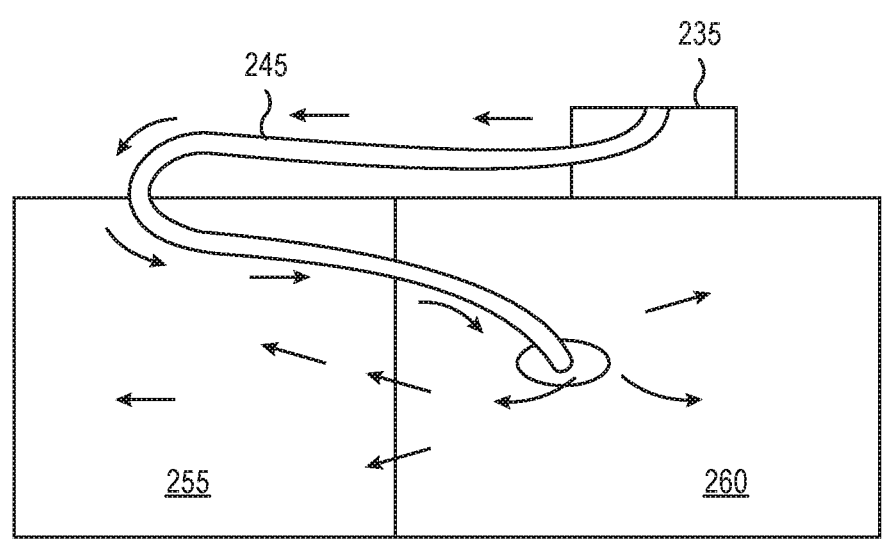

In addition to sanitizing the contents of interior 230, the activated ozone and/or UV light travels through tubing 10 into humidifier 255 (illustrated in FIG. 9c) and CPAP chamber 260 (also illustrated in FIG. 9c), as shown by the arrows of FIG. 9c. The generator will continue to produce UV light and/or activated oxygen for a pre-set period of time until the respiratory assembly has been sufficiently sterilized. Thus, the enclosure acts as a closed-loop system by generating activated oxygen and/or UV light to sanitize CPAP equipment without releasing the activated oxygen and/or UV light into the air surrounding the enclosure. To facilitate sanitizing process, the enclosure can be equipped with one or more air flow mechanisms that assist circulation of the activated oxygen and/or UV light. Residual activated oxygen and/or UV light that remains in the system naturally reverts back into breathable air within a designated time period (e.g., 2 hours). After the sanitizing has completed, the CPAP equipment will be ready to use.

In some embodiments, the sanitizing enclosure starts automatically after the user places the equipment within interior 230 and closes lid 225. Alternatively, the sanitizing can be delayed by programming a desired later time. In some embodiments, enclosure 200 can include an indicator light that will illuminate during the sanitizing process to signify to the user that sanitizing process is ongoing. Lid 225 can remain locked during sanitizing to prevent the user from unintentional exposure to the UV light and/or activated oxygen. At the end of the sanitizing, the lid can automatically unlock in one embodiment.

Sanitizing enclosure 200 can kill about 99% of mold, bacteria, and viruses in the CPAP user's sockets (or mask), tubing, humidifier, and CPAP chamber. In addition to being highly effective, the sanitizing enclosure is designed for ease of use. Users simply place their sockets or mask in the sanitizing enclosure, close the lid, and walk away. Importantly, no disassembly of the CPAP apparatus is required prior to start of the sanitizing process. Advantageously, the sanitizing enclosure can be used daily. In one embodiment, the sanitizing enclosure is configured to support several sanitization cycles to be carried out per day.

As illustrated in FIG. 9c, enclosure 200 can be permanently attached to a CPAP unit including CPAP chamber 260, such as through the use of mechanical elements (screws, bolts, hooks, pins, and the like), adhesives, etc. In some embodiments, the enclosure can be formed as part of a CPAP unit (i.e., the enclosure is built into the CPAP design). However, the presently disclosed subject matter also includes embodiments wherein enclosure 200 can be removably attached to the CPAP unit (e.g., via snap-fit, magnetic attachment, friction fit) or is configured as a stand-alone element.

Although depicted as rectangular-shaped in the Figures, enclosure 200 can be configured in any desired shape, such as circular, oval, square, triangular, oval, hexagonal, pentagonal, star, abstract, and the like.

The enclosure can be configured in any desired size. In some embodiments, the enclosure can have a relatively small size, compared to the size of the CPAP assembly. For example, the enclosure can have a height, width, and depth of less than about 5 inches, such as no more than about 5.0, 4.75, 4.5, 4.25, 4.0, 3.75, 3.5, 3.25, 3.0, 2.75, 2.5, 2.25, 2.0, 1.75, 1.5, 1.25, or 1.0 inches. However, enclosure 200 can have any desired size to accommodate a particular CPAP element within its interior.

What is claimed is:

1. An oral assembly comprising:
    an internal plate curved arcuately to fit in between teeth and lips of a patient, wherein the internal plate comprises an upper segment and a lower segment connected via a hinge to allow movement of each segment in relation to the other;
    an external plate curved arcuately to be positioned directly adjacent to an external surface of a mouth of the patient;
    a passageway extending through the internal plate and the external plate, wherein the passageway is releasably connected to a tubing that is connected to a fluid source; and
    a gasket in fluid connection to the passageway, the gasket comprising an aperture that connects to the tubing connected to the fluid source.

2. The oral assembly of claim 1, wherein the internal plate is molded with an impression of top teeth, bottom teeth, or both the top teeth and the bottom teeth of the patient.

3. The oral assembly of claim 1, wherein the passageway extends through an approximate center portion of the internal plate and the external plate.

4. The oral assembly of claim 1, wherein the assembly lacks straps, masks, or both.

5. The oral assembly of claim 1, wherein the upper segment is molded to correspond to a shape of upper teeth of the patient, the lower segment is molded to correspond to a shape of lower teeth of the patient, or both.

6. The oral assembly of claim 1, further comprising a cushion is adapted to be positioned between the external plate and the external surface of the mouth of the patient.

7. The oral assembly of claim 6, wherein the cushion is constructed from foam or silicone material.

8. The oral assembly of claim 6, wherein the cushion has a central opening passing therethrough.

9. The oral assembly of claim 1, wherein the gasket is adapted to be positioned adjacent to the external plate, external to the patient's mouth.

10. The oral assembly of claim 9, wherein the gasket comprises a swivel ring that allows connection to a fluid source, wherein the swivel ring allows the fluid source to swivel when connected.

11. The oral assembly of claim 1, wherein the swivel ring comprises two branches, each branch including a socket positioned at a distal end.

12. A respiratory assembly comprising:
    a nasal assembly comprising:
        branched tubing connected to sockets through which a fluid is dispensed;
        a pair of posts, each post comprising:
            a flange sized and shaped to fit over a nostril of a patient;
            a main body comprising a passageway configured therein;
            a connector with a central opening sized and shaped to cooperate with one of the receptacles; and
    an oral assembly comprising:
        an internal plate curved arcuately to fit in between teeth and lips of a patient, wherein the internal plate comprises an upper segment and a lower segment connected via a hinge to allow movement of each segment in relation to the other;
        an external plate curved arcuately to be positioned directly adjacent to an external surface of a mouth of the patient;
        a passageway extending through the internal plate and the external plate,
        wherein the passageway is releasably connected to a gasket that is connected to a fluid source, the gasket in fluid connection to the passageway,
        wherein the gasket is in fluid connection to the branched tubing of the nasal assembly.

* * * * *